United States Patent
Im

(10) Patent No.: US 11,826,016 B2
(45) Date of Patent: Nov. 28, 2023

(54) EXTERNAL LIGHT INTERFERENCE REMOVAL METHOD

(71) Applicant: MEDIT CORP., Seoul (KR)

(72) Inventor: Sung Bin Im, Seoul (KR)

(73) Assignee: MEDIT CORP., Seoul (KR)

(*) Notice: Subject to any disclaimer, the term of this patent is extended or adjusted under 35 U.S.C. 154(b) by 394 days.

(21) Appl. No.: 17/161,665

(22) Filed: Jan. 29, 2021

(65) Prior Publication Data

US 2021/0243382 A1    Aug. 5, 2021

(30) Foreign Application Priority Data

Jan. 31, 2020   (KR) .................... 10-2020-0012059

(51) Int. Cl.
| | |
|---|---|
| *A61B 1/00* | (2006.01) |
| *G06T 7/90* | (2017.01) |
| *A61C 9/00* | (2006.01) |
| *G06T 5/50* | (2006.01) |
| *H04N 9/77* | (2006.01) |

(Continued)

(52) U.S. Cl.
CPC ........ *A61B 1/000095* (2022.02); *A61C 9/006* (2013.01); *G06T 5/50* (2013.01); *G06T 7/90* (2017.01); *H04N 9/77* (2013.01); *H04N 23/71* (2023.01); *H04N 23/76* (2023.01); *G06T 2207/20224* (2013.01); *G06T 2207/30036* (2013.01)

(58) Field of Classification Search
CPC ....... A61B 1/000095; G06T 7/90; G06T 5/50; G06T 2207/20224; G06T 2207/30036; H04N 23/76; H04N 23/71; H04N 9/77; A61C 9/006

USPC ......................................................... 382/167
See application file for complete search history.

(56) References Cited

U.S. PATENT DOCUMENTS

| | | | | |
|---|---|---|---|---|
| 2007/0076975 A1* | 4/2007 | Abe | ....................... | H04N 23/76 |
| | | | | 348/E5.079 |
| 2007/0140539 A1* | 6/2007 | Katsumata | ................ | G01J 3/02 |
| | | | | 382/128 |

(Continued)

FOREIGN PATENT DOCUMENTS

| | | |
|---|---|---|
| CN | 10-4159034 A | 11/2014 |
| JP | 2004-195151 A | 7/2004 |

(Continued)

OTHER PUBLICATIONS

Non-final office action dated Dec. 19, 2022 from the Chinese Patent Office for Chinese Application No. 201110123471.1.

(Continued)

*Primary Examiner* — Michael R Neff
(74) *Attorney, Agent, or Firm* — INSIGHT LAW GROUP, PLLC; Seung Lee

(57) ABSTRACT

A method for removing external light interference according to the present disclosure includes: performing the scan in the state where external light is turned on, performing the scan in the state where the external light and internal light are turned on together, and calculating a brightness value from an obtained image. Further, by subtracting the brightness value obtained in the brightness calculating step from a color value of the image through an operation, it is possible to obtain an image and a three-dimensional scan model with the influence of the external light being minimized.

13 Claims, 14 Drawing Sheets

(51) Int. Cl.
    *H04N 23/71*    (2023.01)
    *H04N 23/76*    (2023.01)

(56)          References Cited

U.S. PATENT DOCUMENTS

2012/0287442  A1    11/2012   Tsuyuki
2014/0118539  A1     5/2014   Ota et al.
2014/0320605  A1    10/2014   Johnson
2017/0285907  A1*   10/2017   Li ...................... G06F 3/04847
2021/0140763  A1*    5/2021   Pesach ..................... A61B 1/06

FOREIGN PATENT DOCUMENTS

JP      2005-205147  A     8/2005
JP      2007-190370  A     8/2007
JP      2008-228193  A     9/2008
JP      2012-251997  A    12/2012
JP      2014-089081  A     5/2014
JP      2016-503509  A     2/2016
JP      2017-009351  A     1/2017
KR   10-2018-0073189  A    7/2018
KR      2018-0073189  A    7/2018
KR   10-2019-0103833  A    9/2019
WO      2019/207588  A2   10/2019

OTHER PUBLICATIONS

Non-final office action dated Mar. 1, 2022 from the Japanese Patent Office for Japanese Application No. 2021-013129.
Extended Search Report dated Jun. 25, 2021 from European Patent Office for European Patent Application No. 21154257.6.
Non-final office action dated Jul. 12, 2023 from the Chinese Patent Office for Chinese Application No. 201110123471.1.

* cited by examiner sc1 sc1'

FIG. 11
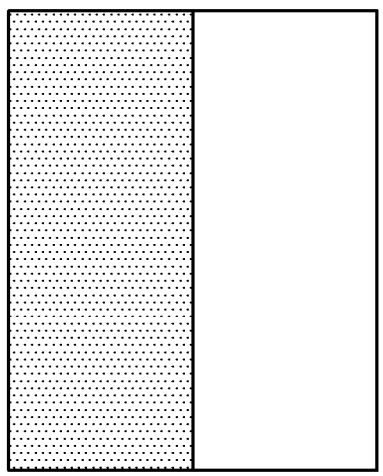
(a)
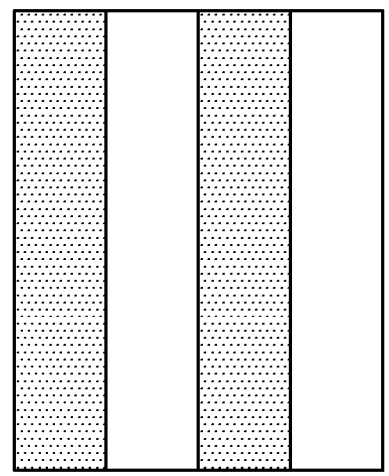
(b)
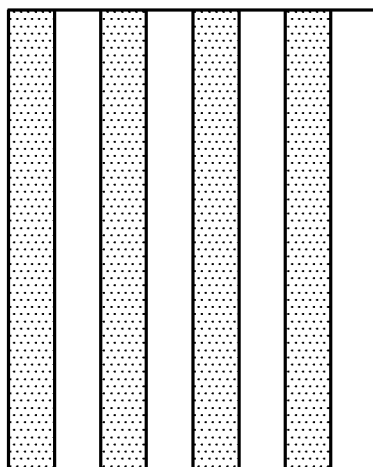
(c)
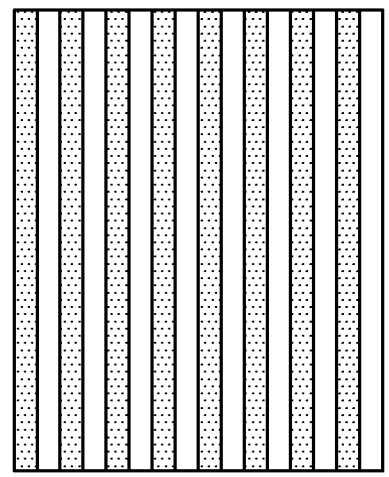
(d)

EXTERNAL LIGHT INTERFERENCE REMOVAL METHOD

CROSS-REFERENCE TO RELATED APPLICATION

This application claims priority to Korean Patent Application No. 10-2020-0012059, filed on Jan. 31, 2020, which is incorporated herein by reference in their entirety.

BACKGROUND OF THE DISCLOSURE

Field of the Disclosure

The present disclosure relates to a method for removing external light interference.

Description of Related Art

In recent years, the use frequency of a three-dimensional scanning technology is being increased in a technical field of scanning the inside of an oral cavity of a patient to provide a prosthetic therapeutic product. Conventionally, the impression is obtained using an alginate or the like in order to produce a plaster cast, and a prosthetic therapeutic product suitable for the oral cavity of the patient based on the produced plaster cast is produced and provided. The implant, the crown treatment, or the like is performed according to such a process of producing the prosthetic therapeutic product. In such a process of producing the prosthetic therapeutic product, the conventional plaster cast has a problem of not precisely expressing the inside of the oral cavity of the patient, and particularly, there is a problem of not precisely obtaining the data for a portion where an abutment is placed on a gingiva, a margin portion of the neighbor teeth, or the like.

To solve such a problem, a handheld type intraoral scanner is rising. The intraoral scanner is directly inserted into the oral cavity of the patient and operated to scan a real oral cavity to be implemented as a three-dimensional scan model. Further, there is an advantage in that the intraoral scanner may freely adjust an angle, which may be used when performing the scan, and a distance between the intraoral scanner and a target (may mean teeth, gingiva, or the like) which is a scan target, thereby having the high degree of freedom of scan.

Meanwhile, a light source introduced from the outside may affect the scanned result if a process of scanning the oral cavity by the scanner is not performed in a darkroom, and the scanned result obtained by the light source is likely to appear slightly different from the result desired by the user. Such a situation may cause a problem of not obtaining the precise data according to any external environment even through the intraoral scanner.

RELATED ART DOCUMENT

Patent Document (Patent Document 1) Korean Patent Application Laid-Open No. 10-2019-0103833

SUMMARY OF THE DISCLOSURE

An object of the present disclosure is to provide a method for removing external light interference for obtaining more precise image or scan data by removing the influence of brightness on the scan according to the external light through an operation process.

The technical objects of the present disclosure are not limited to the aforementioned technical objects, and other technical objects not mentioned may be clearly understood by those skilled in the art from the following descriptions.

A method for removing external light interference according to the present disclosure may include: obtaining color information of a scan target to which internal light is radiated, obtaining brightness information of the scan target by external light in the state where the internal light is turned off, and correcting the color information based on the brightness information.

Further, the correcting of the color information may subtract the brightness value of the brightness information from the color value of the color information.

Further, the color value and the brightness value may be assigned for each pixel of a scan image, and the correcting of the color information may subtract the brightness value from the color value for each pixel.

Further, the obtaining of the brightness information may obtain the brightness information in the state whether the internal light is turned off.

Further, the obtaining of the brightness information may obtain the brightness information from a pattern of the internal light.

Further, the brightness information may be obtained from a dark portion of the pattern.

Further, the pattern may be radiated multiple times in the form in which the dark portion varies, and the brightness information may be obtained from the pattern radiated multiple times.

Further, the method for removing the external light interference may further include: generating a notification signal when the brightness information is a reference value or more.

Further, the brightness value of the brightness information may be assigned for each pixel of the scan image, and when the number of pixels with the brightness value of a threshold or more is a predetermined number or more, the notification signal may be generated.

Meanwhile, a method for removing external light interference according to another exemplary embodiment of the present disclosure may include: obtaining a first data for implementing a three-dimensional scan model, obtaining a second data for calculating a brightness value by external light, and correcting the first data based on the brightness value obtained from the second data.

Further, the first data may include: a first image for implementing a color obtained in the state where internal light is radiated and a second image for implementing a three-dimensional shape, the second data may include: a third image obtained in the state where the internal light is not radiated, and the correcting the first data may apply a corrected color, which is obtained by subtracting a brightness value obtained from the third image from a color value obtained from the first image, to the three-dimensional shape obtained from the second image.

Further, the correcting the first data may subtract a brightness value for each pixel of the third image corresponding to a pixel of the first image from a color value for each pixel of the first image.

Further, the first image to the third image are two-dimensional images obtained for implementing one three-dimensional frame.

Further, the method for removing the external light interference may further include: generating a feedback when the brightness value obtained from the second data is a preset threshold or more.

Further, the second data may include: a third image obtained in the state where the internal light is not radiated, and the method for removing the external light interference may further include: generating a feedback when the number of pixels with the brightness value for each pixel of the third image being a preset threshold or more is a predetermined number or more.

By using the method for removing the external light interference according to the present disclosure and the apparatus using the same, it is possible to prevent the scan of the inside of the oral cavity from being disturbed by the interference of the external light other than the light radiated for scanning the inside of the oral cavity by the scanner, and to obtain the precise scan data.

Further, by informing the scanner user of the determination result through the signal when it is determined that the normal scan is impossible because the external light is extremely strong, it is possible for the user to reduce the influence of the scan by the external light, thereby not having to perform the re-scan due to obtaining the data which is not precise.

Further, it is possible to subtract the brightness value due to the external light prior to producing the three-dimensional scan model, thereby obtaining the three-dimensional scan model with the influence of the external light being minimized.

BRIEF DESCRIPTION OF THE DRAWINGS

FIG. 11 is a diagram illustrating patterns of the internal light radiated to the scan target in the method for removing the external light interference according to the present disclosure.

DESCRIPTION OF SPECIFIC EMBODIMENTS

Figure 1:
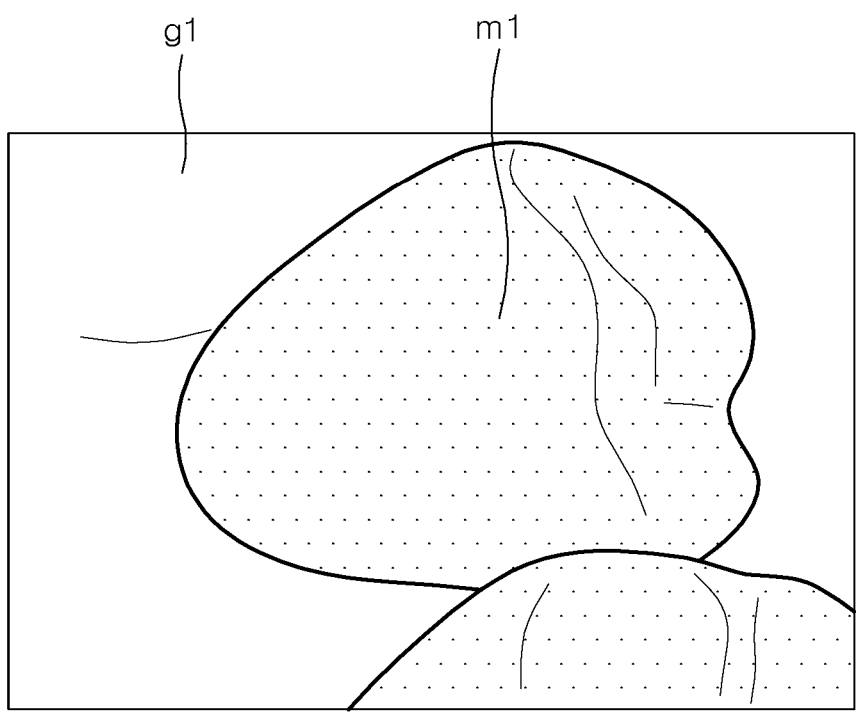
FIG. 1 is a diagram for explaining the state where the photographing for a prosthetic therapeutic product made of a metallic material is performed together with the external light.

Hereinafter, some exemplary embodiments of the present disclosure will be described in detail through exemplary drawings. In adding reference numerals to the components in each drawing, it should be noted that the same components are denoted by the same numerals as possible even if they are indicated in different drawings. Further, in describing the exemplary embodiment of the present disclosure, if it is determined that a detailed description of a related known configuration or function obstructs the understanding of the exemplary embodiment of the present disclosure, the detailed description thereof will be omitted.

In describing the components of the exemplary embodiment of the present disclosure, terms such as first, second, A, B, (a), and (b) may be used. These terms are only for distinguishing the component from other components, and the nature, order, or sequence of the component is not limited by the term. Further, unless otherwise defined, all terms used herein, including technical or scientific terms, have the same meaning as commonly understood by those skilled in the art to which the present disclosure pertains. Terms as defined in a commonly used dictionary should be interpreted as having a meaning consistent with the meaning of the related technology on the context and should not be interpreted as an ideal or excessively formal meaning unless explicitly defined in the present application.

Meanwhile, in obtaining data for brightness and color such as a color value obtained in a step of obtaining color information, a brightness value obtained in a step of obtaining brightness information, and a brightness value obtained in a step of calculating the brightness, which will be described later, various color space expression methods may be used. At least one of various color space expression methods, such as gray (achromatic brightness expression), RGB additive color mixture, HSV (conic), HSV (cylindric), and CMYK and YCbCr models, may be selected and used. However, for the convenience of description, a method for obtaining the brightness value or the color value is described as using the RGB additive color mixture method or the HSV method in the present specification below.

Figure 2:
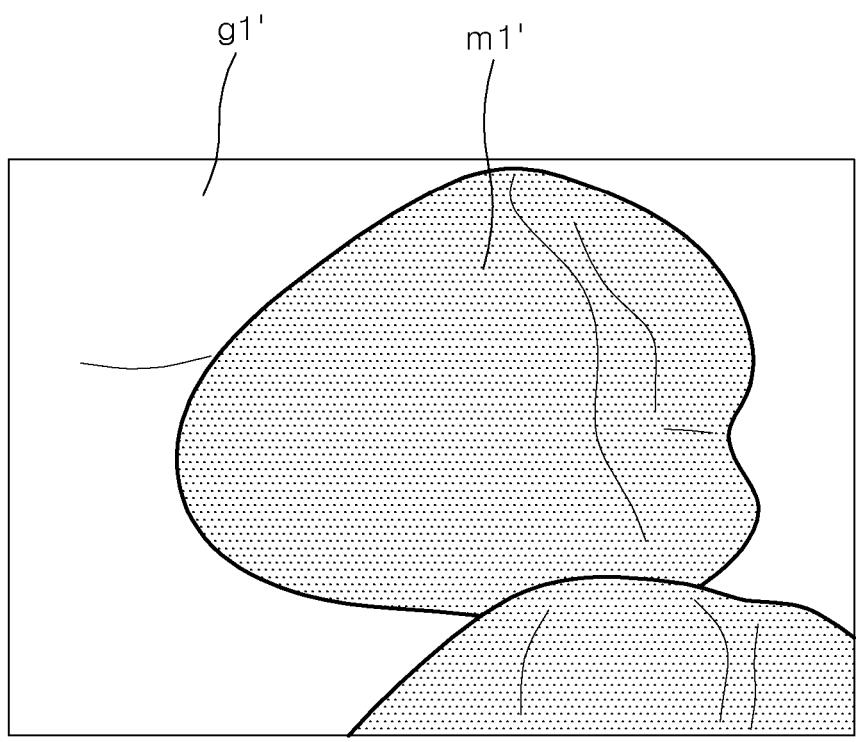
FIG. 2 is a diagram for explaining the state where the photographing for the prosthetic therapeutic product made of the metallic material is performed excluding the external light.

FIG. 1 is a diagram for explaining the state where the photographing for a prosthetic therapeutic product made of a metallic material is performed together with the external light, and FIG. 2 is a diagram for explaining the state where the photographing for the prosthetic therapeutic product made of the metallic material is performed excluding the external light.

Referring to FIG. 1, the user may directly scan the inside of an oral cavity of the patient. Alternatively, the user may obtain the impression for the oral cavity of the patient, as necessary, and scan a plaster cast obtained by obtaining the impression. At this time, the user may use a handheld type scanner to directly scan the inside of the oral cavity of the patient. Further, the handheld type scanner may also be used to scan the plaster cast, but a table type scanner, which disposes the plaster cast on a tray to rotate or tilt the corresponding tray to scan the plaster cast, may also be used. Meanwhile, in the present specification, unless specially mentioned, the 'scanner' may mean a handheld type intraoral scanner.

As illustrated in FIGS. 1 and 2, in the image obtained when scanning a plaster cast on which a prosthetic therapeutic product made of a metallic material is placed, FIG. 1 brightly illustrates the image as a whole and FIG. 2 relatively darkly illustrates the image. This is caused by a difference due to the influence of the external light, and here, the external light means the light serving as other external cause rather than the light radiated by the scanner itself in a space in which the scan operation is performed. For example, the external light may be a lighting lamp included in a unit chair on which the patient sits during dental treatment, or an indoor lighting such as a fluorescent lamp installed on a place performing the scan.

When comparing a gingiva (g1) photographed together with the external light with a gingiva (g1') without the external light removed, and a prosthetic therapeutic product (m1) photographed together with the external light and a prosthetic therapeutic product (m1') without the external light removed, respectively, the images (g1', m1') without the external light removed are relatively dark compared to the images (g1, m1) photographed together with the external light but express the color and brightness substantially closer to the real images, and if the light is seriously reflected in the prosthetic therapeutic product, it is difficult to precisely scan the prosthetic therapeutic product, such that it is important to minimize the influence of the reflected light on the image.

Figure 3:
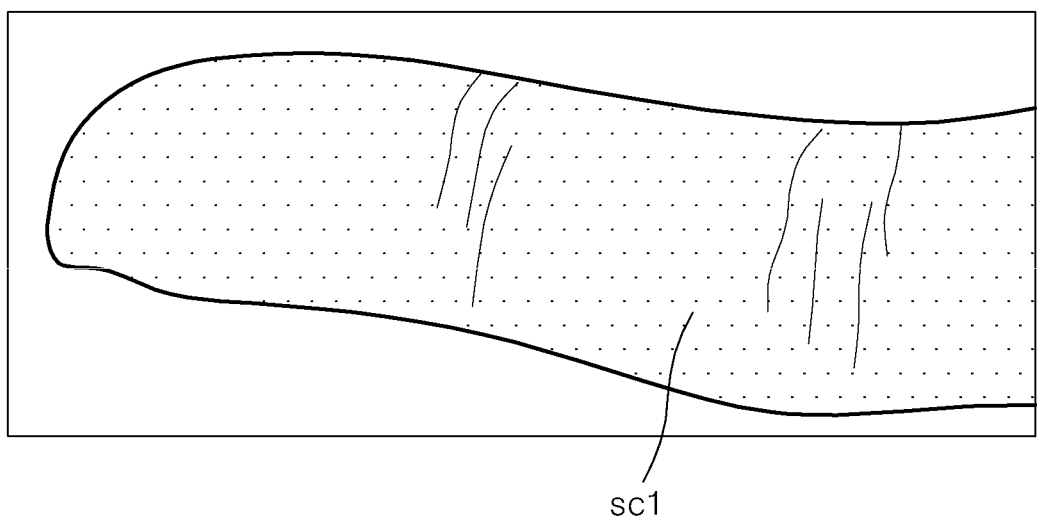
FIG. 3 is a diagram for explaining the state where the photographing is performed together with the external light using a finger as an exemplary photographing target.
Figure 4:
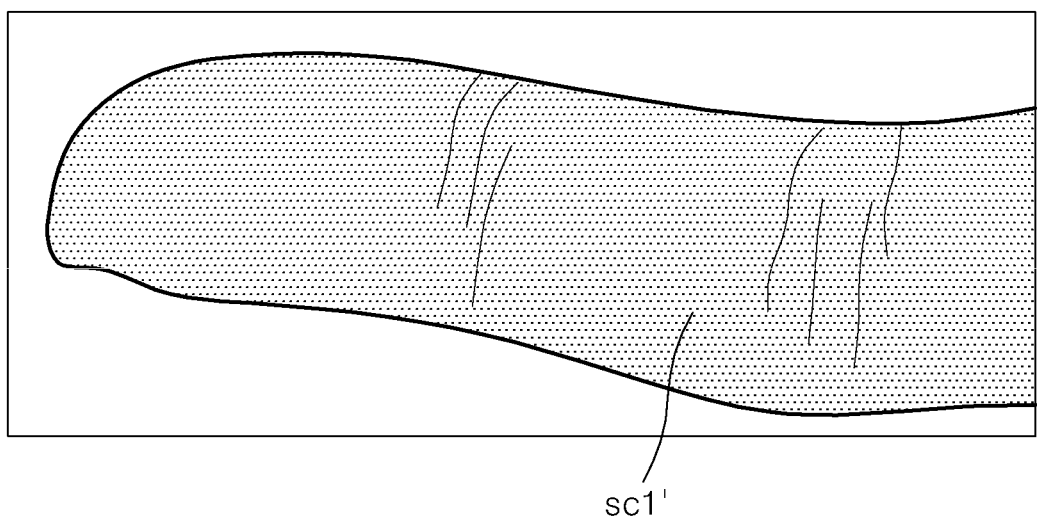
FIG. 4 is a diagram for explaining the state where the photographing is performed excluding the external light using the finger as the exemplary photographing target.

FIG. 3 is a diagram for explaining the state where the photographing is performed together with the external light using a finger as an exemplary photographing target and FIG. 4 is a diagram for explaining the state where the photographing is performed excluding the external light using the finger as the exemplary photographing target.

Referring to FIGS. 3 and 4, it is possible to confirm the influence of the external light from the result of scanning any finger as an exemplary photographing target through a scanner. When comparing a finger (sc1) scanned together with the external light and a finger (sc1') without the external light removed, the finger (sc1') without the external light removed illustrated in FIG. 4 is expressed as the color and brightness close to the real finger, and the image of the finger (sc1) scanned together with the external light illustrated in FIG. 3 is brightly expressed as a whole. Further, the image of the finger (sc1) scanned together with the external light may have a region having a predetermined color at the bottom end thereof, and the color and brightness of the image of the finger (sc1) scanned together with the external light may be different from those of the real finger.

Figure 5:
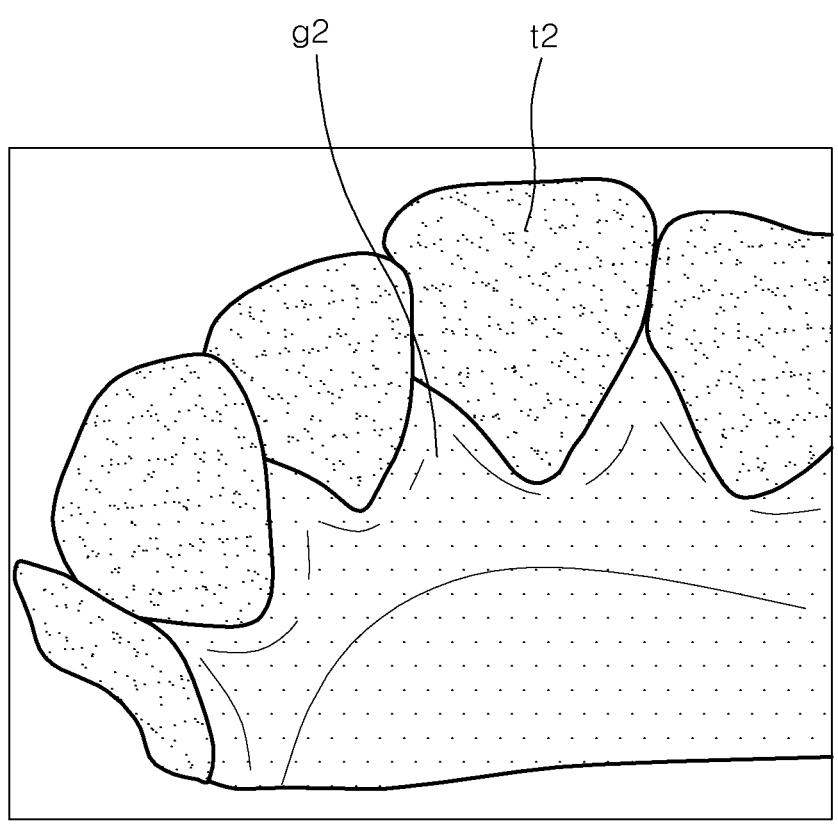
FIG. 5 is a diagram for explaining the state where the scan is performed together with the external light using the inside of an oral cavity as the exemplary scan target.
Figure 6:
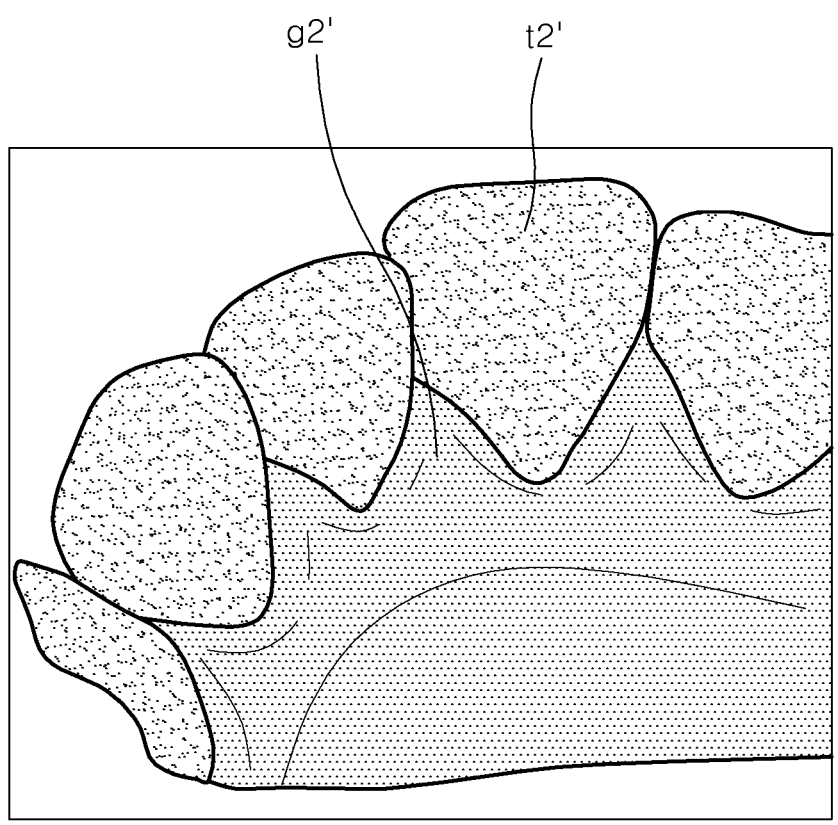
FIG. 6 is a diagram for explaining the state where the scan is performed excluding the external light using the inside of the oral cavity as the exemplary scan target.

FIG. 5 is a diagram for explaining the state where the scan is performed together with the external light using the inside of an oral cavity as the exemplary scan target and FIG. 6 is a diagram for explaining the state where the scan is performed excluding the external light using the inside of the oral cavity as the exemplary scan target.

Referring to FIGS. 5 and 6, the influence of the external light on the image when the inside of the oral cavity is the exemplary scan target may be confirmed by the comparison. A gingiva (g2) and a tooth (t2) scanned together with the external light illustrated in FIG. 5 are relatively brightly expressed when compared with a gingiva (g2') and a tooth (t2') without the external light removed illustrated in FIG. 6. Further, in FIG. 5, a portion where data is not precisely collected on the top of the tooth (t2) scanned together with the external light is also found, and the portion represents the state where the scanned data are insufficiently collected by the influence of the external light.

Figure 7:
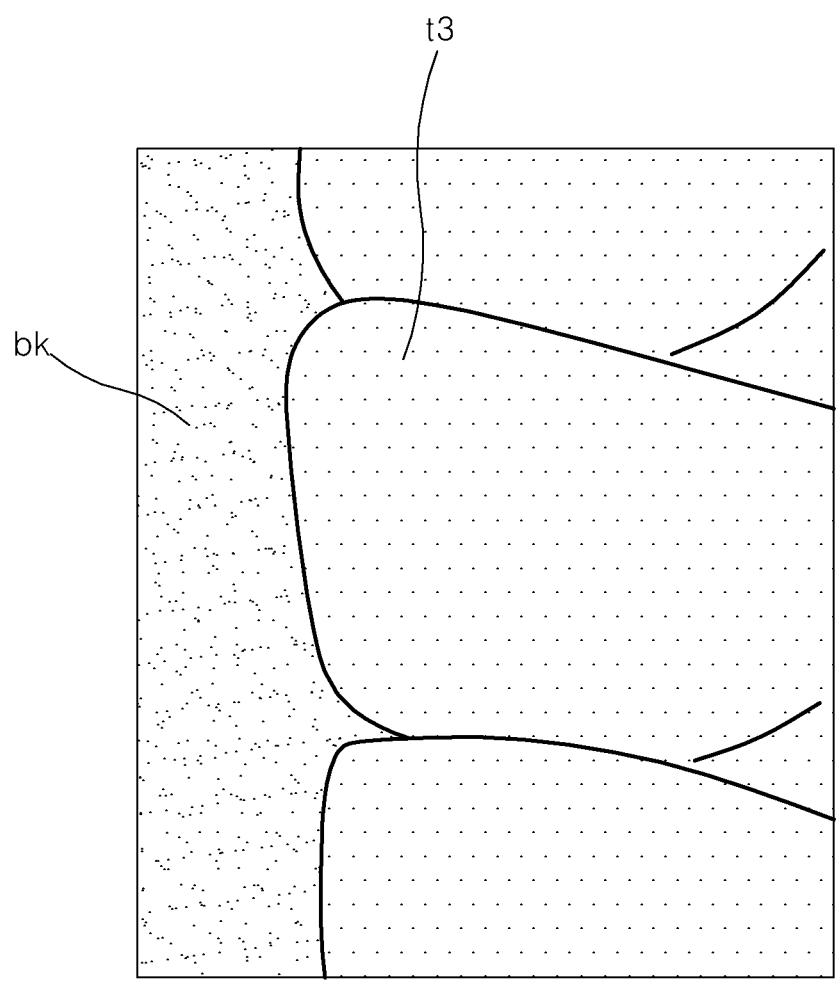
FIG. 7 is a diagram for explaining the state where the scan is performed together with the external light using the inside of the oral cavity as the exemplary scan target.
Figure 8:
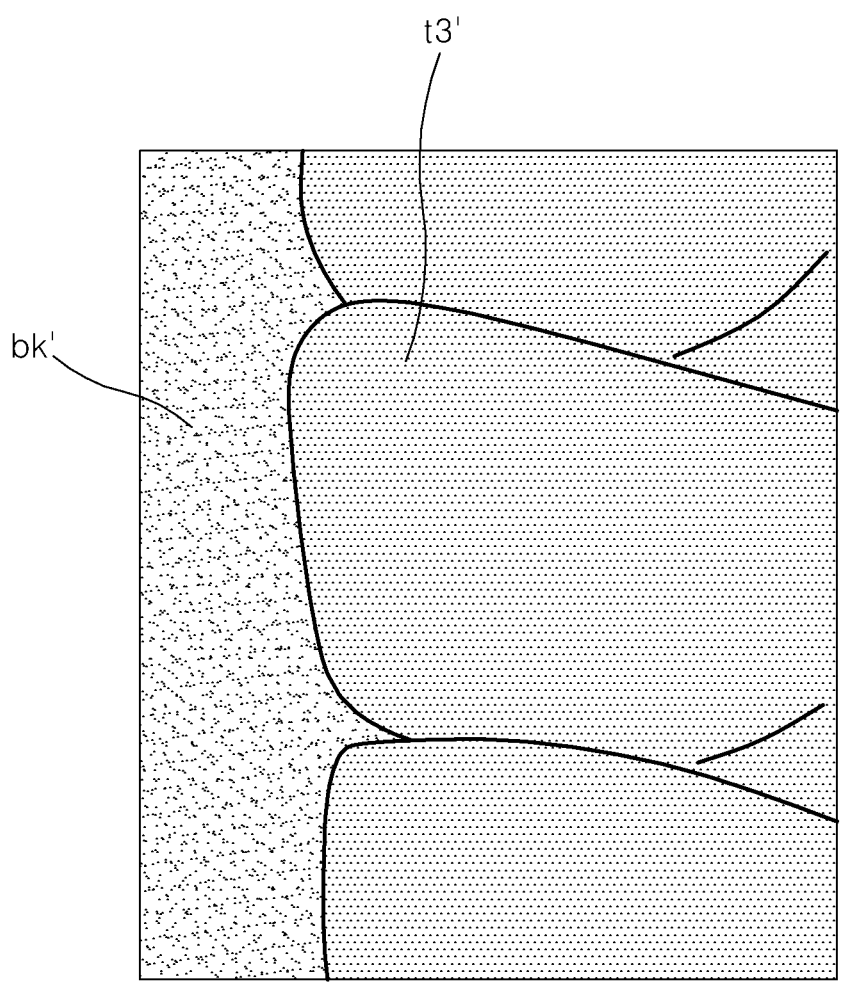
FIG. 8 is a diagram for explaining the state where the scan is performed excluding the external light using the inside of the oral cavity as the exemplary scan target.

FIG. 7 is a diagram for explaining the state where the scan is performed together with the external light using the inside of the oral cavity as the exemplary scan target and FIG. 8 is a diagram for explaining the state where the scan is performed excluding the external light using the inside of the oral cavity as the exemplary scan target.

FIGS. 7 and 8 illustrate the results that the front surface and background of the teeth are scanned. A background (bk) and a tooth (t3) scanned together with the external light illustrated in FIG. 7 may relatively have the fluorescent light when compared with a background (bk') and a tooth (t3') without the external light removed illustrated in FIG. 8. Meanwhile, it may be seen that the real teeth have the color and brightness close to those illustrated in FIG. 8 rather than those illustrated in FIG. 7, and in FIG. 7, the color and brightness of the tooth are distorted by the external light.

Figure 9:
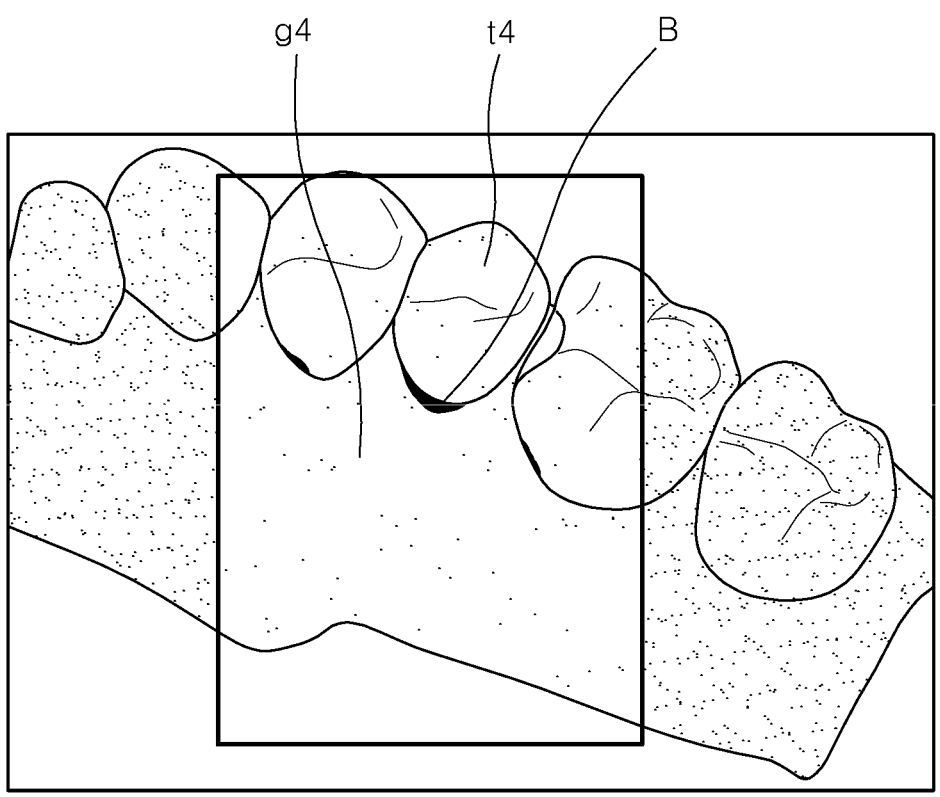
FIG. 9 is a diagram for explaining the scan result when an intraoral cast is scanned by artificially applying the external light.

FIG. 9 is a diagram for explaining the scan result when an intraoral cast is scanned by artificially applying the external light.

FIG. 9 illustrates scan data obtained when scanning a cast, which imitates the inside of the real oral cavity of the human (at this time, this cast has the gingiva of a bright red color or a pink color, and the tooth of an ivory color and indicates the cast modeling the real gingiva and tooth). As the result of scanning only a region (A) indicated by a rectangle by applying the external light, relatively bright and fuzzy gingiva (g4) and tooth (t4) appear as the scanned result when compared with other regions adjacent to the corresponding region. Further, if the external light is serious, a data blank (B) in which the data are missing between the gingiva (g4) and the tooth (t4) is also likely to be generated.

To obtain the precise image or scan data from the aforementioned descriptions and the referred drawings, it is required to minimize the influence (interference) due to the external light. However, there is a problem in that the scan difficulty is increased if the user uses only the internal light generated by the scanner. Therefore, there is a need for a method capable of automatically removing the color interference due to the external light from the image obtained in the state where the external light is turned on.

Figure 10:
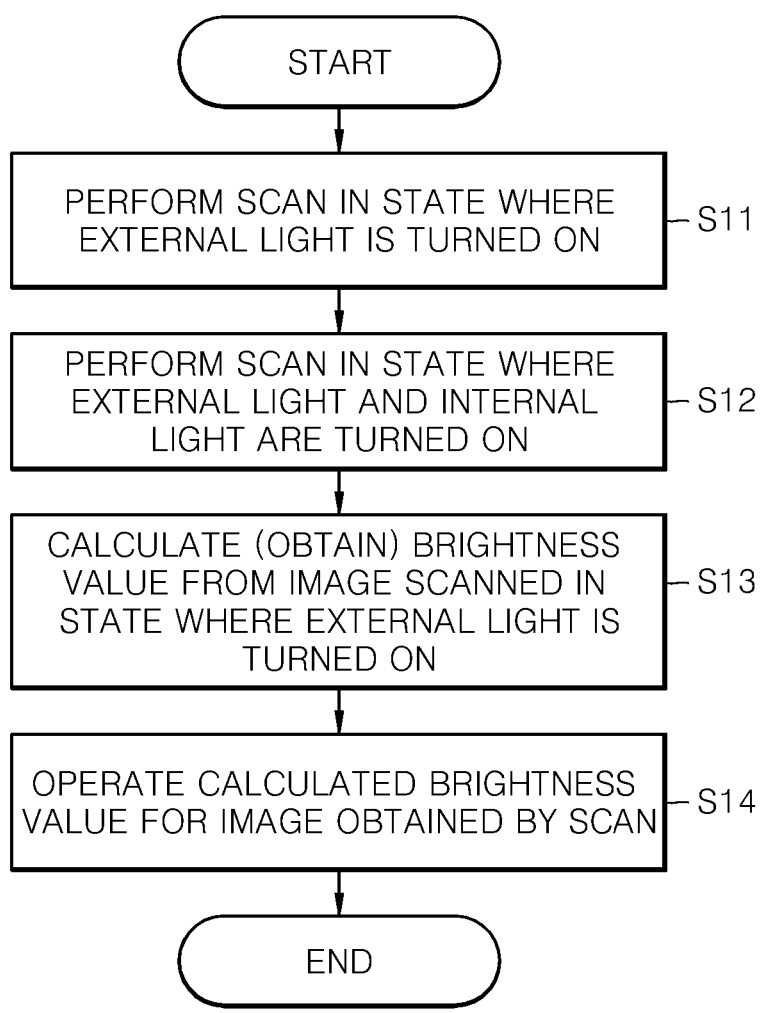
FIG. 10 is a flowchart of a method for removing external light interference according to the present disclosure.

FIG. 10 is a flowchart of the method for removing the external light interference according to the present disclosure.

Referring to FIG. 10, provided is the method for removing the external light interference for solving the aforementioned problems due to the external light. The method for removing the external light interference according to the present disclosure may include a first scan step (S11) of performing the scan through the scanner in the state where the external light is turned on and a second scan step (S12) of performing the scan through the scanner in the state where the internal light together with the external light is turned on. The user performs the scan in the environment where only the external light affects, when scanning the inside of the oral cavity of the patient or the intraoral cast. At this time, there is no light radiated by the scanner, and the information collected in the first scan step (S11) is used to calculate a brightness value due to the external light. A brightness calculating step (S13) will be described later.

Meanwhile, the scanner may include a case inserted into or withdrawn from the inside of the oral cavity and formed with an opening opened such that the figure inside the oral cavity is incident therein in the form of light through one end and a scan unit formed to be coupled to the inside of the case and for accommodating the incident light to generate an image. The case may be formed to protect the internal components of the scanner from the external physical shock or the like, and the case may include a body case, which is the portion gripped by the user, and a tip case, which is the portion inserted into or withdrawn from the inside of the oral cavity to directly contact the oral cavity of the patient.

The inside of the case is formed with the scan unit configured such that the light reflected from the scan target is accommodated inside the scanner to generate the image. The scan unit may include at least one camera and an imaging sensor electrically connected to the camera. The camera accommodates the light incident into the scanner, and the imaging sensor analyzes the accommodated light to generate the image from the accommodated light. At this time, the image may be a two-dimensional image or a three-dimensional image. As an example, the imaging sensor may be a CMOS sensor or a CCD sensor, but is not limited thereto, and may be any configuration capable of generating the image from the light accommodated inside the scanner.

Meanwhile, the scanner may further include a radiation unit formed to be coupled to the inside of the case and for emitting the internal light through the opening. The radiation unit may generate the internal light in order for the scanner itself to illuminate the inside of the oral cavity, and the radiation unit may include a light projector for generating the internal light.

Various forms of light may be used as the internal light generated by the radiation unit. As an example, the light having the wavelength of the visible light region may be used as the internal light. Further, the internal light may be radiated in the form of structural light, which is the specific pattern form, in order to transform the image obtained by the scan unit into a three-dimensional scan model, and the structural light may be generated by the configuration such as a digital micromirror device (DMD).

The brightness value of the image may be obtained from the image obtained by the scan of the scanner in the first scan step (S11) (the brightness calculating step (S13)). At this time, the obtained brightness value may be obtained for the entire region configuring the image obtained in the first scan step (S11), and the form of the obtained brightness value may be the form of the integer between 0 and 255. Meanwhile, the brightness value at this time may correspond to a V value in the HSV method. Further, the brightness value may correspond to a value in the Gray method. As an example, the brightness calculating step (S13) may divide the image obtained in the first scan step (S11) in units of pixel and obtain the brightness value for each pixel.

When the brightness value is obtained from the brightness calculating step (S13) and the image is obtained by a scanner 100 in the state where the external light and the internal light are applied together in the second scan step (S12), the brightness value for the obtained image is operated (an operating step (S14)). At this time, the "operating" the brightness value may mean that the brightness value for the image is processed by the mathematical operation. As an example, the operating step (S14) may subtract the brightness value obtained in the brightness calculating step (S13) from the color values of the respective pixels configuring the image obtained in the second scan step (S12). More specifically, if the brightness value obtained in the brightness calculating step (S13) is X and the color value obtained in the second scan step (S12) is (R, G, B) in any pixel, the color value of the corresponding pixel after the operating step (S14) may be represented as (R-X, G-X, B-X). Meanwhile, the aforementioned R, G, B may correspond to the integer between 0 and 255, respectively.

Meanwhile, the R-X, G-X, and B-X may be represented as the integer between 0 and 255, respectively. Further, in the case of using the HSV method rather than the RGB additive color mixture method, the brightness is represented as the V value, and as a result, operated in the form such as (H, S, V-X), and this is transformed into the RGB form again and then may also be used to implement the three-dimensional scan model. At this time, the X value may be a value representing a gradually brighter brightness as it has a larger value between 0 and 255.

Meanwhile, the aforementioned method for removing the external light interference has been described as first performing the scan in the state where the external light is turned on and the internal light is turned off, and then performing the scan later in the state where the external light and the internal light are turned on together. However, the method for removing the external light interference is not necessarily limited to such a scan order. As an example, a step of obtaining the color information of the scan target to which the internal light is radiated may be preferentially performed, and then a step of obtaining the brightness information of the scan target due to the external light in the state where the internal light is turned off may be performed, and then a step of correcting the color information based on the obtained brightness information may be performed.

The color information of the scan target to which the internal light is radiated may be obtained by the RGB additive color mixture method or the HSV method, and the brightness information of the scan target due to the external light in the state where the internal light is turned off may also be obtained by the same method as in the aforementioned brightness calculating step (S13). According to the obtained color information and brightness information, it is possible to subtract the brightness value of the brightness information from the color value of the color information to correct the color information. At this time, the color value of the color information and the brightness value of the brightness information may be assigned for each pixel of the scanned image, and the process of correcting the color information may also be performed for each pixel of the scanned image. The corrected pixel may have the corrected color value and the corrected image may be displayed with the influence of the external light being minimized.

Meanwhile, in the step of obtaining the brightness information of the scan target, when the brightness information is a reference value or more, a step of generating a notification signal may be added. As an example, the brightness information is collected in the state where only the external light affects in the state where the internal light is turned off, and the brightness value of the collected brightness information is collected for each pixel of the obtained image in the scan process. At this time, if the number of pixels with the brightness value collected for each pixel being 200 or more is about 50% or more of the number of all pixels, it is possible to generate the notification signal indicating that the influence of the external light is strongly acting such that the scanner user may perceive such a situation. However, the values presented as the reference values in the present specification are illustrative and such values may be reset and used according to the user's needs.

The user may perceive the fact that the influence of the external light is strongly acting by the notification signal and take measures such as turning off the external light or reducing the illumination of the lighting. Further, the external light may also be systematically removed in the step of correcting the color information, and as described above, the influence of the external light may be physically blocked, thereby improving the reliability of the scan data.

The aforementioned step of generating the notification signal may also be performed together with the operating step of correcting the color by the external light, but the color correction and the notification signal generation may not be essentially performed at the same time. As an example, when the scan is performed in the state where the internal light and the external light are simultaneously applied, the process of correcting the color by subtracting the brightness value calculated in the brightness calculating step from the color value may be stopped according to the brightness information. More specifically, the process of correcting the color may be stopped if the brightness information is the reference value or more and only a signal requiring the user to reduce the external light may be generated. It is possible to prevent the use of the unnecessary resource by stopping the process of correcting the color while generating the notification signal, and it is possible to prevent the unnecessary data from being stored by stopping the scan of the portion into which the external light is excessively incident.

Further, as described above, the step of generating the notification signal may also stop the operating step (the process of correcting the color by subtracting the brightness value from the color value) while generating the notification signal if the brightness information is the reference value or more but may also determine whether to perform the operating step according to the brightness value calculated in the brightness calculating step without performing the operating step from the beginning. As an example, if the obtained brightness value for each pixel is the value or more presented as the reference value, the notification signal may be generated without performing the operating step.

Meanwhile, the brightness information of the scan target by the external light may also be obtained from the pattern (this may mean the structural light) of the internal light in the state where all of the internal light and the external light are turned on (acting). At this time, the pattern of the internal light may have various forms for obtaining the depth information of the scan target, and as an example, the pattern may be the pattern having the stripe form appearing by alternating a bright portion and a dark portion. The brightness information may be obtained from the dark portion of the pattern, such a dark portion may be radiated multiple times (n times) in the form of a variable pattern, and the brightness information may be obtained from the dark portion of the pattern radiated multiple times (n times). To obtain the color information of the scan target, as described above, the scanner may have the radiation unit capable of radiating the internal light toward the scan target inside the scanner.

When the light is output by the light projector formed on the radiation unit, the output light may form various patterns by the process of performing the accommodation, the reflection, or the like by the ON/OFF states of each of a plurality of mirrors configuring the digital micromirror device (DMD). At this time, the mirror in the ON state reflects the accommodated light to be radiated to the scan target to form the bright portion and the mirror in the OFF state forms the dark portion such that the accommodated light is not reflected. Therefore, the portion (the bright portion) of the scan target corresponding to the mirror in the ON state is affected by all of the internal light and the external light and the portion (the dark portion) of the scan target corresponding to the mirror in the OFF state is affected by only the external light (the portion of the scan target corresponding to the mirror in the OFF state is not radiated with the internal light to be relatively dark when compared with the portion of the scan target corresponding to the mirror in the ON state, such that such a portion is named the dark portion of the pattern).

FIG. 11 is a diagram illustrating the patterns of the internal light radiated to the scan target in the method for removing the external light interference according to the present disclosure.

Referring to FIG. 11, the pattern of the internal light may be radiated multiple times (n times) in various forms such as a binary code and a gray code. For example, if the pattern of the internal light according to the binary code is radiated, the light having the stripe form illustrated in FIGS. 11A to 11D may be sequentially radiated. At this time, the black portion of the left in FIG. 11A may be referred to as the dark portion and the white portion of the right in FIG. 11A may be referred to as the bright portion. For the same purpose, in FIG. 11B, the internal light may be formed such that the dark portion-the bright portion-the dark portion-the bright portion from the left may alternately appear and radiated to the scan target. As described above, the pattern is radiated to the scan target n times in the form in which the dark portion varies, thereby obtaining the brightness information (the integer between 0 and 255) for all pixels of the portion corresponding to the scan target region.

Hereinafter, a method for removing the external light interference according to another exemplary embodiment of the present disclosure will be described.

Figure 12:
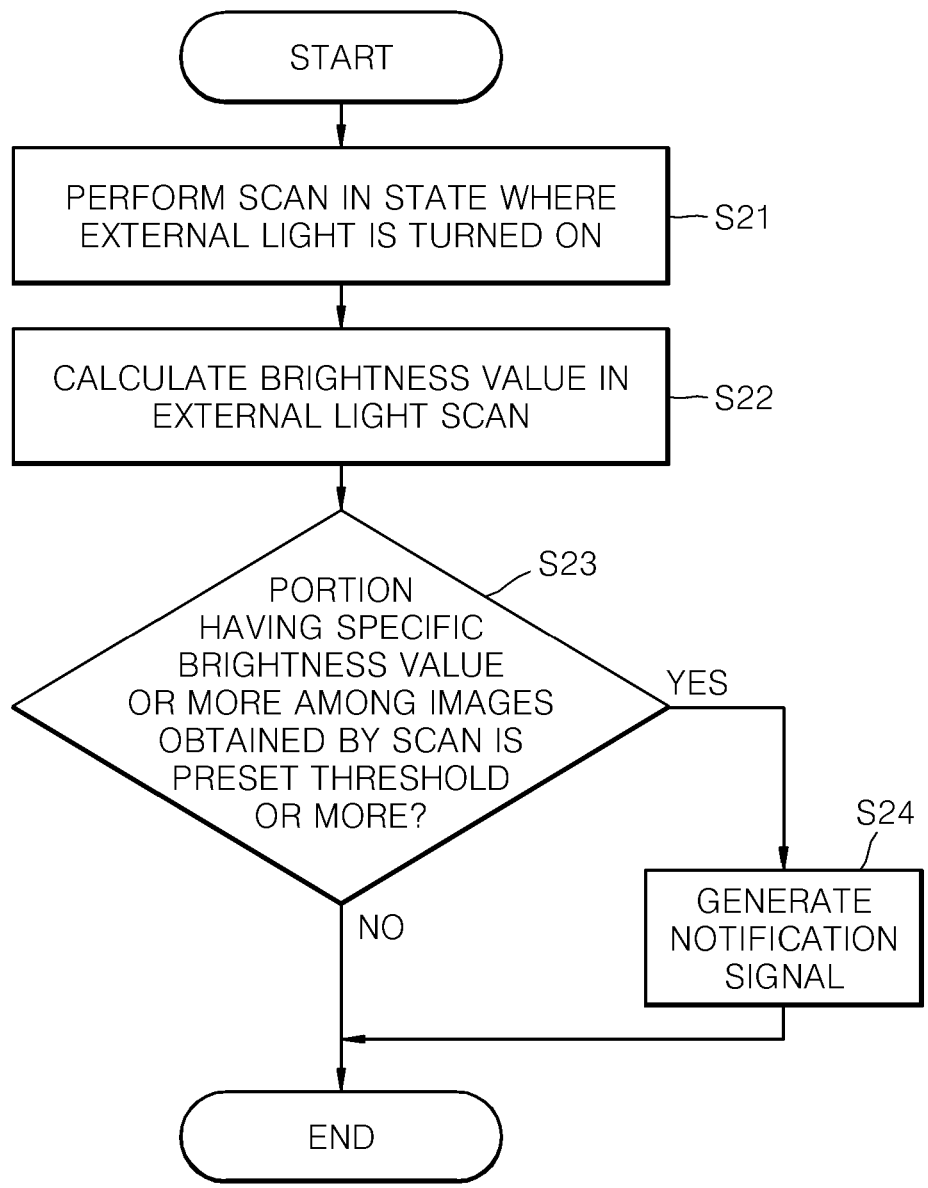
FIG. 12 is a flowchart illustrating a method for removing the external light interference according to another exemplary embodiment of the present disclosure.

FIG. 12 is a flowchart illustrating the method for removing the external light interference according to the present disclosure.

Referring to FIG. 12, the method for removing the external light interference according to the present disclosure may include a scan step (S21) of performing the scan by the scanner 100 in the state where the external light is turned on, the brightness calculating step (S22) of obtaining the brightness value from the image obtained by the scan in the scan step (S21), and a determining step (S23) of determining whether a portion having the brightness value of a specific brightness value (reference brightness value) or more is a set value or more from the brightness values obtained in the brightness calculating step (S22). The scan step (S21) scans the inside of the oral cavity of the patient or the intraoral cast by the scanner 100 in the state where the external light is turned on. At this time, if the internal light is tuned off, the scan step (S21) may be performed in the same process as that of the aforementioned first scan step (S11) and if the internal light is turned on, the scan step (S21) may be performed in the same process as that of the aforementioned second scan step (S12). Preferably, the scan step (S21) may perform the scan in the state where all of the external light and the internal light are turned on.

The brightness calculating step (S22) is the same method as that of the aforementioned brightness calculating step (S13) and obtains the color information for each pixel by dividing the image obtained in the scan step (S21) in units of pixel using the RGB additive color mixture method or the HSV method. At this time, the bright portion may be counted to the reference brightness value or more for the obtained color. The region having the reference brightness value or more may mean the region having the specific portion or more in the RGB additive color mixture method and mean the region having a reference V value or more in the HSV method.

Meanwhile, if the portion having the brightness value of the reference brightness value or more has a set value or more, the determining step (S23) may be performed to generate an alarm notification signal (notification generating step (S24)). At this time, the alarm notification signal may be operated by various methods. The alarm notification signal may be the vibration by an actuator embedded in the scanner or may also be an alarm sound generated by a speaker while being electrically connected to the operation unit performing the determining step (S23) and may also be a guidance message displayed on a screen by a display unit electrically connected to the operation unit and formed to be spaced apart from the scanner. Alternatively, the alarm notification signal may also be generated by two or more means among them. According to the generation of the alarm notification signal, the user may perceive that the external light excessively affects the scan process and minimize the influence of the external light in the scan process by reducing the intensity of the external light or removing (turning off) the external light.

Hereinafter, a method for removing the external light interference according to still another exemplary embodiment of the present disclosure will be described.

Figure 13:
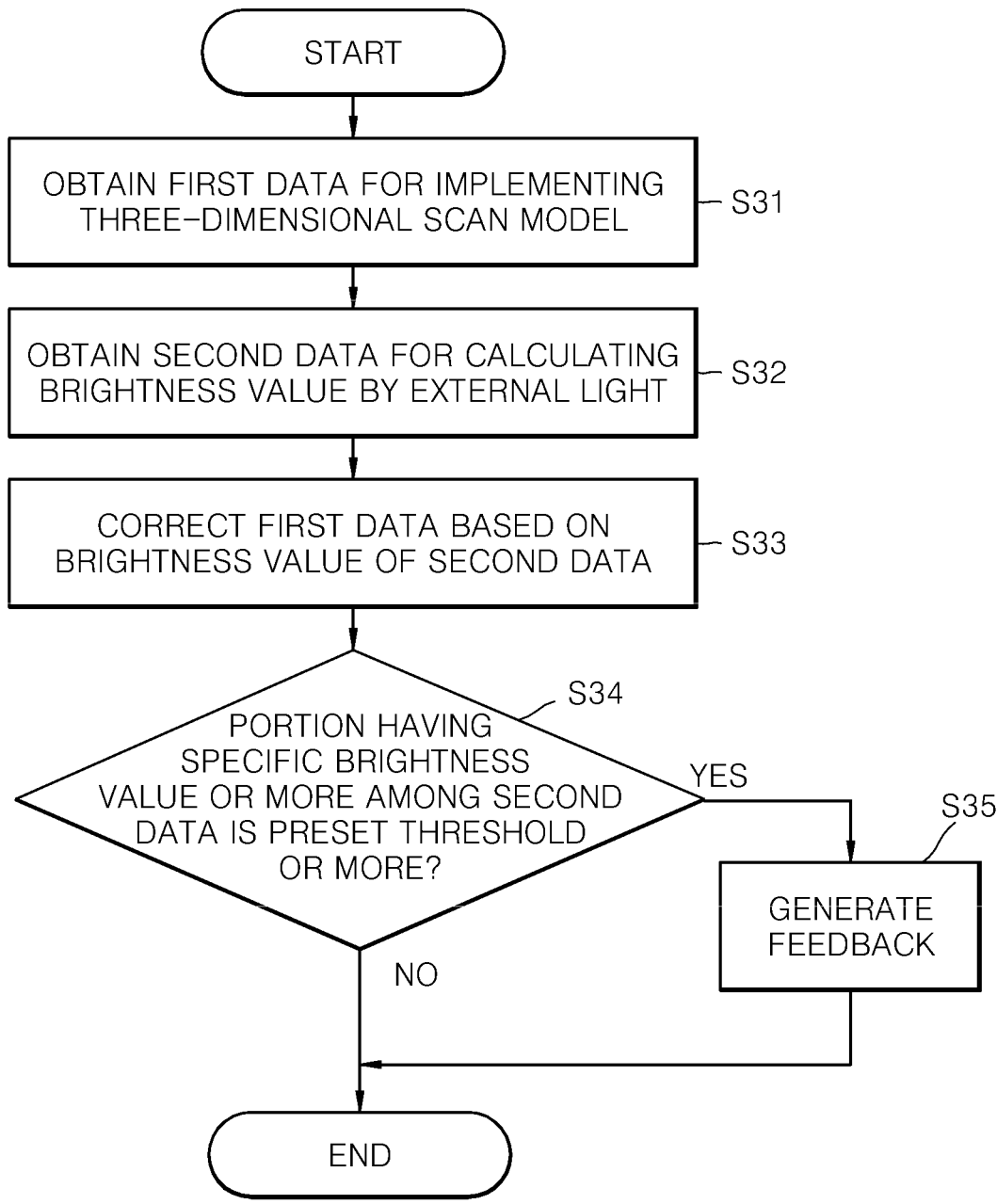
FIG. 13 is a flowchart illustrating a method for removing the external light interference according to still another exemplary embodiment of the present disclosure.

FIG. 13 is a flowchart illustrating a method for removing the external light interference according to still another exemplary embodiment of the present disclosure. Referring to FIG. 13, the method for removing the external light interference according to still another exemplary embodiment of the present disclosure may include obtaining a first data for implementing the three-dimensional scan model (S31), obtaining a second data for calculating the brightness value by the external light (S32), and correcting the first data based on the brightness value obtained from the second data (S33).

The first data and the second data may be obtained in the state where the external light is radiated, and particularly, the first data is used to implement the three-dimensional scan model, such that the internal light (a projector inside the scanner) may be obtained in the state of being radiated together with the external light.

The first data may include a first image for implementing a color and a second image for implementing a three-dimensional shape. At this time, the three-dimensional scan model may be formed by coupling at least one three-dimensional frame by an alignment method such as an iterative closest point (ICP) method. One three-dimensional frame may be implemented by mapping the color value obtained from the first image, which is at least one two-dimensional image, with the three-dimensional shape (for example, point on a three-dimensional space) obtained from the second image, which is at least one two-dimensional image).

Meanwhile, the method for removing the external light interference according to still another exemplary embodiment of the present disclosure may obtain the color information from the first data and obtain the brightness information from the second data. The process of obtaining the color information or obtaining the brightness information has been described above and thus will be omitted.

The correcting of the first data (S33) may correct the first data by subtracting the brightness value obtained from the second data before mapping the color value obtained from the first image with the three-dimensional shape obtained from the second image. Here, the second data may include a third image obtained in the state where the internal light is not radiated. Therefore, the third image may be the two-dimensional image obtained by scanning a subject in the state where only the external light is radiated to the object.

The correcting the first data (S33) will be described more specifically. For the third image, the brightness value (for example, the value between 0 and 255) by the external light for each pixel may be calculated, and the brightness value for each pixel may likewise be subtracted from the color value of the first image calculated for each pixel. That is, the brightness value of the pixel of the third image corresponding to the pixel of the first image is subtracted from the color value of the pixel of the first image. The color value of the pixel of the first image may be calculated by the RGB method, the HSV method, or the like, for example and this has been described above.

One three-dimensional frame may be implemented by applying the color value (i.e., the corrected color value) of the first image subtracted as described above to the three-dimensional shape obtained from the second image. Here, one three-dimensional frame may be implemented as the two-dimensional images obtained during one cycle, that is, the first image to the third image and the order of obtaining the first image to the third image within one cycle is not specially limited.

Further, the process of obtaining the first image to the third image and the process of correcting the color value may also be performed in parallel. As an example, the first image is obtained and then the third image is obtained to correct the color value, and then the corrected color value may be applied to the second image obtained after the third image. As described above, the three-dimensional scan model with the influence of the external light being minimized may be obtained by correcting the color value of the first image based on the brightness value obtained from the third image and applying the corrected color value of the first image to the three-dimensional shape obtained from the second image and the user may provide the optimal treatment to the patient.

Meanwhile, when the brightness value obtained from the third image is a preset threshold or more, a feedback may be generated for the user (S35). As an example, it is determined whether the brightness value calculated from the third image is the preset threshold or more (S34). At this time, if the brightness value calculated from the third image is the preset threshold or more, the notification signal may be generated such that the user may perceive such a situation. Therefore, if lots of external light is incident, the user may reduce the illuminance of the external light, thereby enhancing the quality of the scan data. The notification signal may be generated using at least one of aural, visual, and tactile methods and the type of the notification signal has been described above.

The generation of the feedback may be performed in parallel with the process of correcting of the color value or performed without the process of correcting of the color value, and the determination of whether the feedback is generated has been described, such that the detailed description thereof will be omitted.

Hereinafter, an apparatus using the method for removing the external light interference according to the present disclosure will be described. The contents for the overlapping configuration will be briefly described or omitted.

Figure 14:
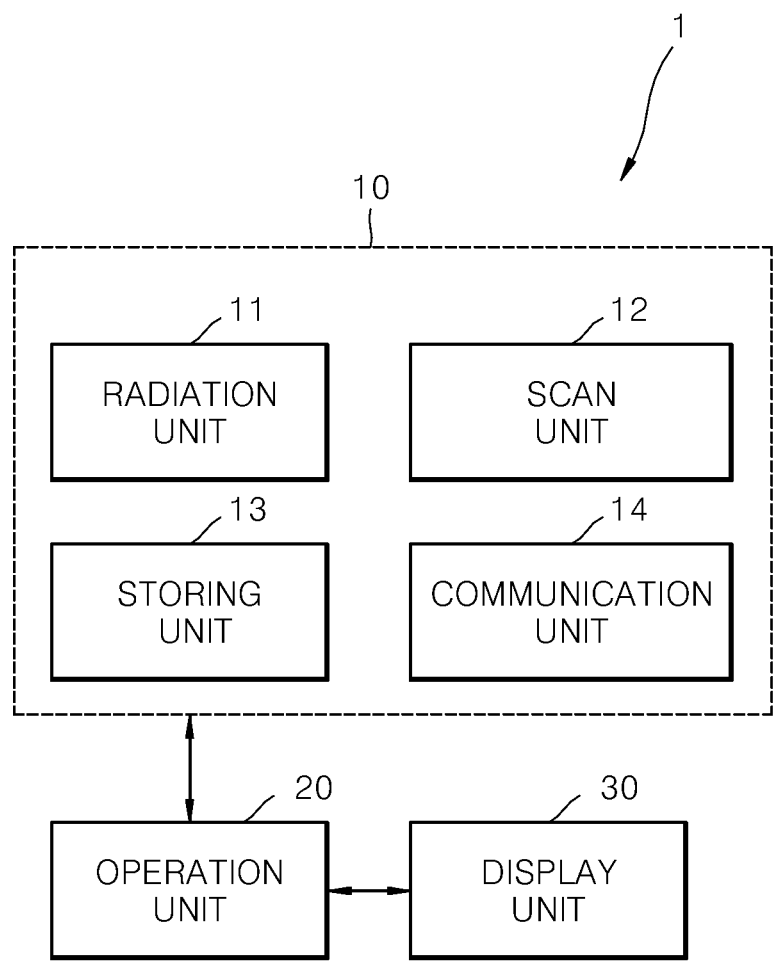
FIG. 14 is a schematic diagram illustrating an apparatus using the method for removing the external light interference according to the present disclosure.

FIG. 14 is a schematic diagram illustrating an apparatus 1 using the method for removing the external light interference according to the present disclosure.

Referring to FIG. 14, an apparatus using the method for removing the external light interference according to the present disclosure may include a case inserted into or withdrawn from the inside of the oral cavity and formed with an opening opened such that the figure inside the oral cavity is incident therein in the form of light through one end, a scan unit 12 formed to be coupled to the inside of the case and for accommodating the light incident therein to generate the image, and an operation unit 20 for performing the operation for the image obtained by the scan unit 12 so as to analyze the image as digital data.

The apparatus using the method for removing the external light interference according to the present disclosure may include a tip case having one end of the case inserted into and withdrawn from the inside of the oral cavity of the patient and being in direct contact with the inside of the oral cavity of the patient, and a body case gripped by the user (the therapist). Further, the inside of the case may be formed with the scan unit 12 including at least one camera and an imaging sensor electrically connected to the camera and the light incident into the case by the scan unit 12 may be accommodated by the camera and generated as the two-dimensional image or the three-dimensional image.

Meanwhile, the generated two-dimensional image, three-dimensional image, or three-dimensional scan model may be stored in a storing unit 13 formed inside the case and transmitted to an operation unit 20 connected through a communication unit 14 by wired or wirelessly. The two-dimensional image or the three-dimensional image temporarily stored in the storing unit 13 may be used for the operation unit 20 to operate the brightness value later.

The operation unit 20 may divide the image (the two-dimensional image or the three-dimensional image) obtained by the scan unit 12 into predetermined interval regions and obtain the brightness value for each region. At this time, the predetermined interval region may be a unit of the pixel. The form of the obtained brightness value may be obtained as the integer between 0 and 255 as described above.

Meanwhile, the apparatus using the method for removing the external light interference may further include a radiation unit 11 coupled and formed inside the case and for emitting the internal light to radiate the inside of the oral cavity. The radiation unit 11 may emit the internal light to illuminate the inside of the oral cavity, and the radiation unit 11 may include a light projector. Further, various forms of light may be used as the internal light emitted by the radiation unit. As an example, the internal light may be the light having the wavelength of the visible light region. The internal light may be radiated in the form of the structural light, which has a specific pattern form, to transform the image obtained by the scan unit 12 into the three-dimensional scan model.

The digital data subjected to the operation for the brightness value by the operation unit 20 may be displayed on a display unit 30 in the form of the three-dimensional scan model. At this time, the operation of the brightness value of the operation unit 20 may mean that the brightness value obtained in the state where only the external light is turned on is subtracted from the brightness value obtained in the state where all of the external light and the internal light are turned on. By the operation of the aforementioned operation unit 20, the three-dimensional scan model displayed on the display unit 30 may be displayed in the form in which the image with the influence of the external light being removed or minimized is transformed in the three dimension and this may allow the user to obtain the precise data for the inside of the oral cavity of the patient.

Meanwhile, the radiation unit 11 and the scan unit 12 may be formed to be coupled to the inside of the case to form the scanner 10, and the operation unit 20 and the display unit 30 may be formed to be spaced apart from the scanner. That is, the scanner 10, the operation unit 20, and the display unit 30 are formed to be electrically connected but may not be inseparably formed. However, if the scanner 10 itself is mounted with a processor having the operation function according to the configuration, the processor performs the function of the operation unit 20, such that the scanner 10 and the operation unit 20 may also be integrally formed.

The aforementioned description is merely to exemplarily describe the technical spirit of the present disclosure, and various modifications and changes will be possible by those skilled in the art to which the present disclosure pertains without departing from the essential characteristics of the present disclosure.

Therefore, the exemplary embodiments disclosed in the present disclosure do not limit the technical spirit of the present disclosure but describe it, and the scope of the technical spirit of the present disclosure is not limited to the exemplary embodiments. The protective scope of the present disclosure should be interpreted by the appended claims, and all technical spirit within the scope equivalent thereto should be interpreted as being included in the scope of the present disclosure.

What is claimed is:

1. A method for removing external light interference, the method comprising:
   obtaining color information of a scan target to which internal light is radiated;
   obtaining brightness information of the scan target by external light;
   generating a notification signal to reduce the intensity of the external light or to remove the external light by user when the brightness information is greater than or equal to a reference value so that the influence of the external light is minimized; and
   correcting the color information based on the brightness information.

2. The method for removing the external light interference of claim 1,
   wherein the correcting of the color information subtracts the brightness value of the brightness information from the color value of the color information.

3. The method for removing the external light interference of claim 2,
   wherein the color value and the brightness value are assigned for each pixel of a scan image, and the correcting of the color information subtracts the brightness value from the color value for each pixel.

4. The method for removing the external light interference of claim 1,
   wherein the obtaining of the brightness information obtains the brightness information in the state whether the internal light is turned off.

5. The method for removing the external light interference of claim 1,
   wherein the obtaining of the brightness information obtains the brightness information from a pattern of the internal light.

6. The method for removing the external light interference of claim 5,
   wherein the brightness information is obtained from a dark portion of the pattern.

7. The method for removing the external light interference of claim 6, wherein the pattern is radiated multiple times in the form in which the dark portion varies, and the brightness information is obtained from the pattern radiated multiple times.

8. The method for removing the external light interference of claim 1,
wherein the brightness value of the brightness information is assigned for each pixel of the scan image, and when the number of pixels with the brightness value of greater than or equal to a threshold is greater than or equal to a predetermined number more, the notification signal is generated.

9. A method for removing external light interference, the method comprising:
obtaining a first data for implementing a three-dimensional scan model;
obtaining a second data for calculating a brightness value by external light;
generating a feedback to reduce the intensity of the external light or to remove the external light by user when the brightness value obtained from the second data is greater than or equal to a preset threshold so the influence of the external light is minimized; and
correcting the first data based on the brightness value obtained from the second data.

10. The method for removing the external light interference of claim 9,
wherein the first data comprises: a first image for implementing a color obtained in the state where internal light is radiated and a second image for implementing a three-dimensional shape,
wherein the second data comprises: a third image obtained in the state where the internal light is not radiated, and
wherein the correcting the first data applies a corrected color, which is obtained by subtracting a brightness value obtained from the third image from a color value obtained from the first image, to the three-dimensional shape obtained from the second image.

11. The method for removing the external light interference of claim 10,
wherein the correcting the first data subtracts a brightness value for each pixel of the third image corresponding to a pixel of the first image from a color value for each pixel of the first image.

12. The method for removing the external light interference of claim 10,
wherein the first image to the third image are two-dimensional images obtained for implementing one three-dimensional frame.

13. The method for removing the external light interference of claim 9,
wherein the second data comprises: a third image obtained in the state where the internal light is not radiated, and
wherein the generating the feedback generates the feedback when the number of pixels with the brightness value for each pixel of the third image being greater than or equal to a preset threshold is greater than or equal to a predetermined number.

* * * * *